United States Patent [19]

McDaniel

[11] Plant 4,172

[45] Dec. 27, 1977

[54] ROSE PLANT—VOLARE VARIETY

[75] Inventor: Gayle Kent McDaniel, Carlton, Oreg.

[73] Assignee: Carlton Rose Nurseries, Inc., Carlton, Oreg.

[21] Appl. No.: 759,542

[22] Filed: Jan. 14, 1977

[51] Int. Cl.[2] ..... A01H 5/00

[52] U.S. Cl. ..... Plt./20

[58] Field of Search ..... Plt./20-21

*Primary Examiner*—Robert E. Bagwill

*Attorney, Agent, or Firm*—Burns, Doane, Swecker & Mathis

[57] ABSTRACT

A rose plant of the Hybrid Tea Class obtained as a seedling from unnamed seed parent No. 2573-V-69 and unnamed pollen parent No. 44-E-66. The rose plant of the new and distinct variety freely yields long lasting small to medium blooms borne on medium length stems on a continuous basis in a greenhouse.

17 Drawing Figures

SUMMARY OF THE INVENTION

The object of the present invention is to provide a hardy rose plant of the Hybrid Tea Class which is capable of freely yielding quality cut flowers under greenhouse conditions.

The variety of rose plant of the present invention was obtained at Hillsboro, Oreg., as a seedling from unnamed seed parent No. 2573-V-69 and unnamed pollen parent No. 44-E-66. The crossing was made on June 2, 1969, sowing on Nov. 15, 1969, and the first flower appeared on Feb. 23, 1970. The new variety was initially designated rose No. 643-E, and subsequently the Volare variety.

Asexual reproduction of my new and distinct variety shows that its unique combination of characteristics come true to form and are established and transmitted through succeeding propagations.

BRIEF DESCRIPTION OF THE DRAWINGS

The accompanying photographs show typical specimens of the vegetative growth and flowers of the new variety in different stages of development and are depicted in color as nearly true as it is reasonably possible to make the same in color illustrations of this character:

FIG. 1 is a view of several flowers in different stages of development;

FIG. 2 is a developing bud with a new growth;

FIG. 3 shows a bud as the calyx breaks;

FIG. 4 shows the flower when starting to open;

FIG. 5 shows the flower when completely opened;

FIG. 6 shows an outer petal, top — inside surface, bottom — outer surface;

FIG. 7 shows an intermediate petal, top — inside surface, bottom — outer surface;

FIG. 8 shows an inner petal, top — inside surface, bottom — outer surface;

FIG. 9 shows a receptacle with the stamens and pistils showing;

FIG. 10 shows a receptacle showing the pistils after removing the stamens;

FIG. 11 shows a mature hip;

FIG. 12 shows one of the leaves with a composition of three leaflets showing the upper surface;

FIG. 13 shows one of the leaves with a composition of five leaflets showing the upper surface;

FIG. 14 shows one of the leaves with a composition of five leaflets showing the under surface;

FIG. 15 shows a portion of a main stem and branching;

FIG. 16 shows branches; and

FIG. 17 shows a new growth and developing bud and upper and under sides of two young leaves.

DETAILED DESCRIPTION OF THE DISCLOSURE

The following description was made during October, 1976 of rose plants of the new and distinct variety growing in greenhouse at Watsonville, Calif. Color designations are to *A Dictionary of Color* by A. Maerz and M. Rea Paul, McGraw-Hill (New York and London — 1930).

Flower:

*Flowers borne.*—Singly to stems; on normal, medium length stems.

*Quantity of bloom.*—Free in greenhouse.

*Continuity.*—Continuous.

*Fragrance.*—Slight; spicy.

*Bud.*—Peduncle: medium length; stiff erect; yellow green; entirely smooth. Before calyx breaks: Size: small. Form: medium; pointed ovoid; with foliaceous appendages on the surface of the bud; with medium cut foliaceous parts extending beyond the tip of the bud equal to ¾ or more of its length. As calyx breaks: Color: Plate 55, L/8, Rubient. As first petal opens: Size: small — medium. Form: pointed ovoid. Color: Outside: Plate 3, J/6 Dark Jack Rose. Inside: Plate 3, L/6 Bright Salvia. Opening: It does open up well. It is retarded from opening by cold weather.

*Bloom.*—Size when fully open: small — medium: 3¼ inches to 3¾ inches. Petalage: very double; from 38 to 44 petals arranged irregularly. Form: high centered; petals at first very tightly rolled outward; becoming later at maturity tightly rolled outward.

*Petals.*—Medium leathery; with inside velvety; outside shiny satiny. Shape: Outer: ovate; with 2 notches. Intermediate: obovate; with 1 tooth. Inner: round; with 1 notch. Color: colors may be modified by being shaded with other colors. Color of newly opened flower: Outer petal: Outside surface: Plate 3, J/6, Jack Rose. Inside surface: Plate 3,L/6, Salvia. Intermediate petal: Outside surface: Plate 3, J/6, Jack Rose. Inside surface: Plate 3, L/5, slightly lighter than Salvia.

Inner petal: Outside surface: Plate 3, K/4, Claret or Bordeaux. Inside surface: Plate 3, L/6, Salvia. Color of flower 3 days after opening: Outer petal: Outside surface: Plate 3, J/6, Jack Rose. Inside surface: Plate 5, L/4, Fez +. Inner petal: Outside surface: Plate 4, J/6, Cerise. Inside surface: Plate 5, K/6, Old Red. General color effect: Newly opened flower: Plate 3, L/6, Salvia. Three days open: Plate 4, L/5, Flaming Maple. Behavior: drop off cleanly. Flower longevity: cut roses grown in greenhouse kept at living room temperature 10 days during October–November.

Reproductive organs:

*Stamens.*—Many; arranged irregularly about pistils.

*Filaments.*—Many; most with anthers; medium. Color: Plate 6, L/8, Dark Cardinal.

*Anthers.*—Open at various times; medium size. Color: Plate, 7, J/12, Chutney. Seldom fused with a petaloid.

*Pollen.*—*Gold.*

*Pistils.*—Very many.

*Styles.*—Uneven; short length; heavy; very loosely bunched.

*Stigma.*—Yellow.

*Ovaries.*—Some protruding from receptacle.

*Hips.*—Pear-shaped; moderately smooth; thick walls. Color: Plate 9, D/12, Chinese Orange.

*Sepals.*—Falling soon; medium-long length; spear-shaped; recurved.

*Seeds.*—Few; medium—large.

Plant:

*Foliage.*—Leaves: compound of 3, 5, and 7; moderately abundant, medium size; heavy leathery wrinkled. Leaflet: Shape: apex acute, base round, margin irregularly serrate. Color: Mature upper surface: Plate 23, H/9, Meadow Green. Mature under surface: Plate 23, H/3, Lichen. Young upper surface: Plate 15, L/5, Roman Green. Young under surface: Plate 7, E/9, Kaffa. Rachis (the supporting stem of compound leaf): light. Upper side: smooth. Under side: moderately prickly. Stipules: medium length; moderately narrow width; medium points; turning out at an angle of more than 45°; recurved toward the stem. Disease: resistance comparable to the average variety growing under the same cultural conditions.

Growth:

*Habit.*—Bushy; upright; much branched.

*Growth.*—Moderate vigor.

*Canes.*—Medium.

*Main stems.*—Dull. Color: Plate 15, L/6, Metallic Green. Prickles: several. Color: Plate 15, L/7, Olive Brown. Hairs: none.

*Branches.*—Bright. Color: Plate 15, L/4, Olive Green. Prickles: several. Color: Plate 14, K/11, Antique Brown. Hairs: none.

*New shoots.*—Dull. Color: Plate 7, H/7, Cedar. Prickles: several, small. Color: Plate 6, K/6, Garnet Red. Hairs: none.

I claim:

1. A new and distinct variety of rose plant of the Hybrid Tea Class obtained as a seedling from unnamed seed parent No. 2573-V-69 and unnamed pollen parent No. 44-E-66 characterized by its ability to yield small to medium-sized long lasting blooms on a continuous basis in a greenhouse substantially as shown and described.

* * * * *

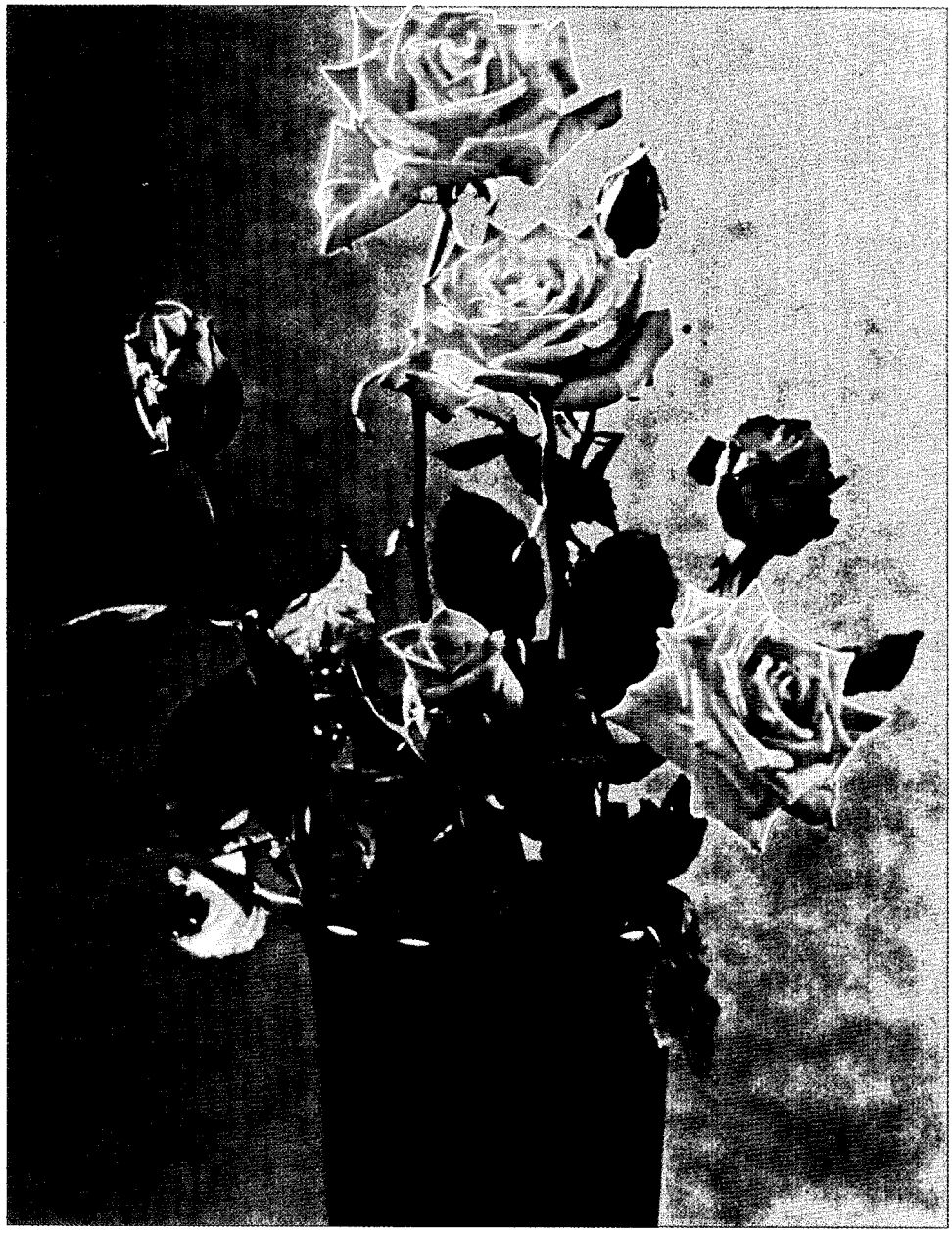

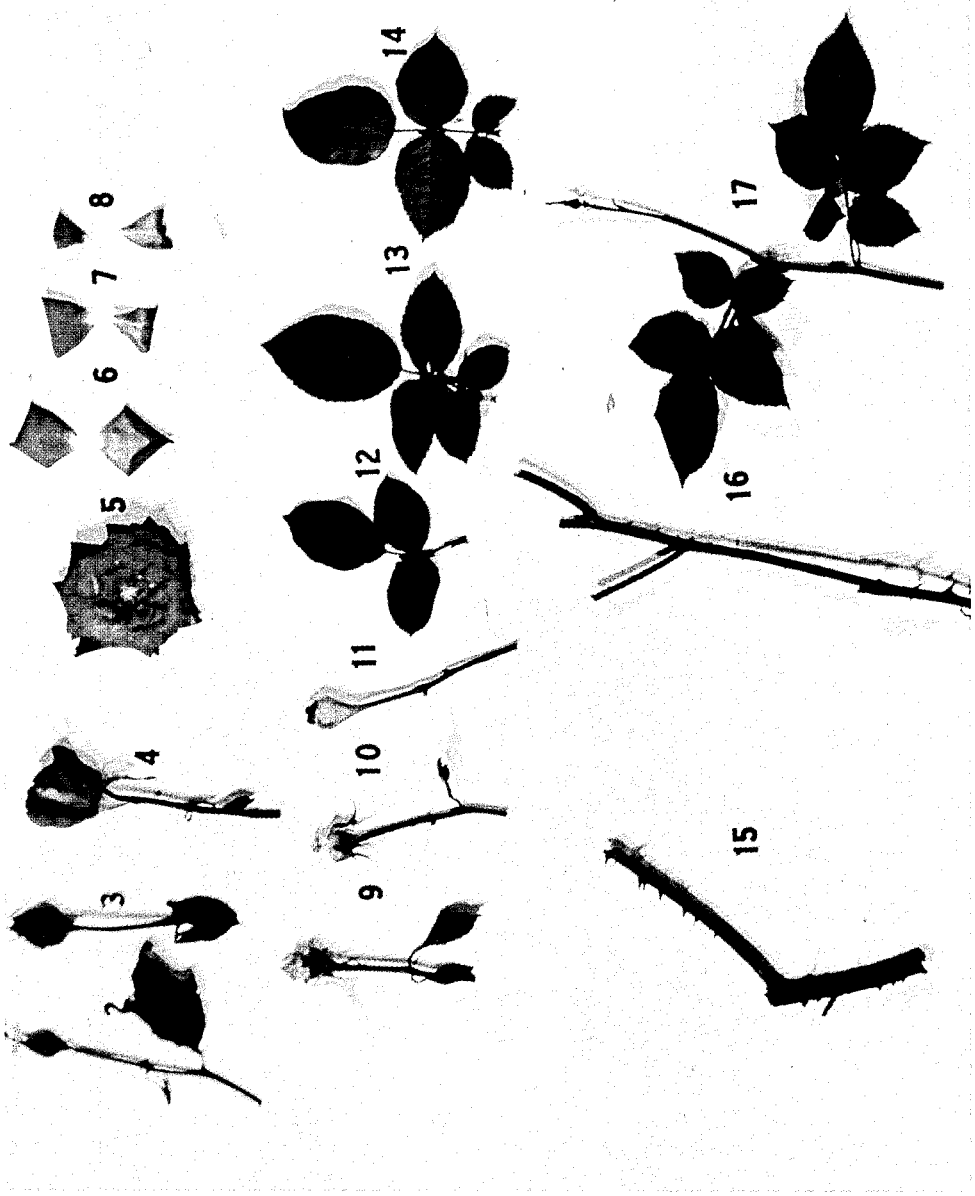
2
3
4
5
6
7
8
9
10
11
12
13
14
15
16
17